United States Patent [19]

Fischer et al.

[11] Patent Number: 4,521,342
[45] Date of Patent: Jun. 4, 1985

[54] PREPARATION OF 2-ALKYL-4,4-DIACYLOXYBUT-2-ENALS

[75] Inventors: Rolf Fischer, Heidelberg; Hans-Martin Weitz, Bad Durkheim; Joachim Paust, Neuhofen, all of Fed. Rep. of Germany

[73] Assignee: BASF Aktiengesellschaft, Ludwigshafen, Fed. Rep. of Germany

[21] Appl. No.: 473,096

[22] Filed: Mar. 7, 1983

[30] Foreign Application Priority Data

Mar. 24, 1982 [DE] Fed. Rep. of Germany ....... 3210706

[51] Int. Cl.³ .......................... C09F 5/08; C09F 7/10; C11C 3/00; C11C 3/02
[52] U.S. Cl. ................................ 260/410; 260/410.6; 260/410.9 N; 560/112; 560/113; 560/121; 560/128; 560/231; 560/234; 560/261; 560/262
[58] Field of Search ..................... 260/410.9 N, 410 R, 260/410.6; 560/262, 112, 113, 121, 128, 231, 234, 261

[56] References Cited

U.S. PATENT DOCUMENTS

| | | | |
|---|---|---|---|
| 4,095,030 | 6/1978 | Stapp .................................. | 560/262 |
| 4,182,901 | 1/1980 | Fozzard et al. ..................... | 560/262 |
| 4,225,727 | 9/1980 | Kamiyama et al. ............... | 260/410.6 |
| 4,284,796 | 8/1981 | Fischer et al. ..................... | 560/262 |
| 4,410,719 | 10/1983 | Fischer et al. ................... | 560/262 X |

FOREIGN PATENT DOCUMENTS

| | | |
|---|---|---|
| 68372 | 1/1983 | European Pat. Off. . |
| 3210084 | 9/1983 | Fed. Rep. of Germany . |
| 3210706 | 10/1983 | Fed. Rep. of Germany . |
| 3210707 | 10/1983 | Fed. Rep. of Germany . |
| 3210705 | 10/1983 | Fed. Rep. of Germany . |

OTHER PUBLICATIONS

Chemical Abstracts 86: 121562u (1976).
Chemical Abstracts 83: 58121v (1975).

Primary Examiner—Helen M. S. Sneed
Attorney, Agent, or Firm—John H. Shurtleff

[57] ABSTRACT

2-alkyl-4,4-diacyloxybut-2-enals of the formula

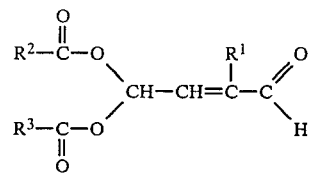

where $R^1$ is alkyl and $R^2$ and $R^3$ are each hydrogen or an aliphatic, cycloaliphatic or aromatic radical, are prepared by a process wherein a 2-alkyl-2,4-diacyloxybut-3-enal of the formula

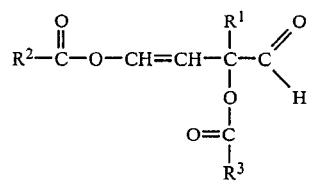

is treated with an aliphatic carboxylic acid.

14 Claims, No Drawings

PREPARATION OF 2-ALKYL-4,4-DIACYLOXYBUT-2-ENALS

The present invention relates to a process for the preparation of 2-alkyl-4,4-diacyloxybut-2-enals by isomerization of a 2-alkyl-2,4-diacyloxybut-3-enal in the presence of an aliphatic carboxylic acid.

It has been disclosed that 3-alkyl-3-acetoxybut-1-enes substituted in the 4-position undergo isomerization in the presence of an acid to give the corresponding 1-acetoxy-3-alkylbut-2-enes (allyl rearrangement). Thus, for example, 3-methyl-3-acetoxy-4-chlorobut-1ene is converted in the presence of sulfuric acid, acetic acid and copper sulfate to 1-acetoxy-3-methyl-4-chlorobut-2-ene (J. Amer. Chem. Soc., 72 (1950), 4608), while 3-methyl-3-acetoxy-4-nitrobut-1-ene is converted in the presence of concentrated sulfuric acid to 1-acetoxy-3-methyl-4-nitrobut-2-ene (J. Org. Chem., 42 (1977), 2939). 3-Alkyl-3-hydroxybut-1-enes which are substituted in the 4-position, for example by chlorine (J. Org. Chem., 44 (1979), 1716), phenyl, vinyl or n-pentyl (Tetrahedron Lett. (1974), 351), can be converted in the presence of acetic acid, acetic anhydride and p-toluenesulfonic acid to the corresponding 1-acetoxy-3-alkylbut-2-enes substituted in the 4-position.

It is an object of the present invention to convert 2-alkyl-2,4-diacyloxybut-3-enals to 2-alkyl-4,4-diacyloxybut-2-enals.

We have found that this object is achieved, and that 2-alkyl-4,4-diacyloxybut-2-enals of the formula

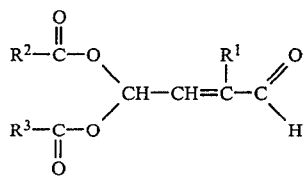

I where $R^1$ is alkyl of 1 to 5 carbon atoms and $R^2$ and $R^3$ are each hydrogen, an aliphatic radical of 1 to 15 carbon atoms, a cycloaliphatic radical of 5 to 7 carbon atoms or an aromatic radical, can be obtained, if a 2-alkyl-2,4-diacyloxybut-3-enal of the formula

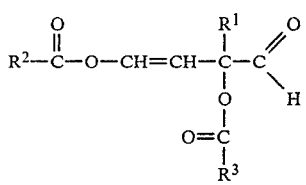

II where $R^1$, $R^2$ and $R^3$ have the above meanings, is treated with an aliphatic carboxylic acid in the absence of strong acids.

Using the novel process, the 2-alkyl-2,4-diacyloxybut-3-enals are converted to the 2-alkyl-4,4-diacyloxybut-2-enals in a reaction step which is technically very simple, the product predominantly comprising the trans compound.

For the preparation of 2-methyl-4,4-diacetoxybut-2-enal, the reaction may be represented by the following equation:

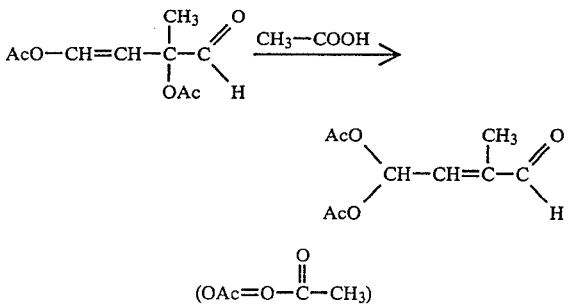

$(OAc = O - \overset{O}{\overset{\|}{C}} - CH_3)$

The 2-alkyl-2,4-diacyloxybut-3-enals of the formula II which are used as starting materials can be prepared by reacting a 2-alkyl-1,4-diacyloxybuta-1,3-diene with an oxygen donor.

In the starting materials of the formula II, alkyl of 1 to 5 carbon atoms is, for example, methyl, ethyl, propyl or butyl, aliphatic radicals of 1 to 15 carbon atoms are, for example, alkyl radicals, eg. methyl, ethyl, n-propyl, i-propyl, n-butyl, i-butyl, palmityl or stearyl, cycloaliphatic radicals are, for example, cyclopentyl, cyclohexyl or cycloheptyl, and a suitable aromatic radical is phenyl. Specific examples of starting materials are 2-methyl-, 2-ethyl-, 2-n-propyl-, 2-butyl- and 2-pentyl-2,4-diacetoxybut-3-ene, 2-methyl-2-acetoxy-4-palmityloxybut-3-ene and 2-methyl-2-acetoxy-4-cyclohexyloxybut-3-ene.

The novel process is carried out in the absence of strong acids, such as mineral acids or sulfonic acids, since these convert the starting materials predominantly to 3-alkyl-2,5-dihydrofuran-2-ones.

Examples of suitable aliphatic carboxylic acids are formic acid, acetic acid, propionic acid, butyric acid, valeric acid, plalmitic acid and stearic acid. The carboxylic acids can also contain water. It is also possible to carry out the reaction in the presence of a solvent which is inert under the reaction conditions, examples of such solvents being carboxylates, eg. methyl acetate, chlorohydrocarbons, eg. methylene chloride, chloroform, carbon tetrachloride and 1,2-dichloroethane, hydrocarbons, eg. alkanes, benzene and alkylbenzenes, and ethers, eg. diethyl ether, tetrahydrofuran and dioxane.

The carboxylic acid employed may contain not more than 20, in particular not more than 5, moles of water per mole of 2-alkyl-2,4-diacyloxybut-3-enal used.

The starting material of the formula II is treated with the carboxylic acid, for example at from 20° to 200° C., in particular from 50° to 120° C., for about 0.5–40 hours. The rearrangement reaction can be carried out under atmospheric or superatmospheric pressure, batchwise or continuously. The treatment mixture advantageously contains from 1 to 20% by weight of the compound undergoing rearrangement.

In order to achieve very high yields of 2-alkyl-4,4-diacyloxybut-2-enals of the formula I, it is advisable to correlate the temperature of the rearrangement reaction, the reaction time, and the concentration of the compound undergoing rearrangement, and where relevant of water, in the carboxylic acid used. Thus, for example, the rearrangement reaction is carried out for a short time where a high temperature is employed.

The novel process is carried out, for example, as follows: The 2-alkyl-2,4-diacyloxybut-3-enal is dissolved in the particular carboxylic acid, and the solution is heated at the temperature required for rearrangement.

After the reaction is complete, the carboxylic acid is distilled off, and the residue is purified by distillation or crystallization.

It was surprising that treatment of the 2-alkyl-2,4-diacyloxybut-3-enals with carboxylic acids gave the desired 2-alkyl-4,4-diacyloxybut-2-enals, since in the presence of strong acids, such as mineral acids or sulfonic acids, 3-alkyl-2,5-dihydrofuran-2-ones are formed.

An advantage of the novel process for the preparation of the compounds of the formula I is that a mixture of a 2-alkyl-2,4-diacyloxybut-3-enal of the formula II with a 2-alkyl-4,4-diacyloxybut-2-enal of the formula I can also be used, such mixtures being extremely difficult to separate by distillation. A further advantage is that the carboxylic acid used and the water can be separated off at the working up stage by distillation, ie. without prior neutralization.

The 2-alkyl-4,4-diacyloxybut-2-enals obtainable by the process are useful intermediates, for example for the preparation of terpenes (German Laid-Open Application DOS No. 2,537,810).

EXAMPLE 1

A mixture of 2.9 g of 2-methyl-2,4-diacetoxybut-3-enal and 1.5 g of 2-methyl-4,4-diacetoxybut-2-enal was dissolved in 50 g of glacial acetic acid, and the mixture was heated for 4 hours at 100° C. The acetic acid was stripped off in a rotary evaporator, and the residue was then distilled (120° C./0.8 mbar) in a ball tube to give 3.0 g (70%, based on methyldiacetoxybutenals employed) of 2-methyl-4,4-diacetoxybut-2-enal, whose structure was confirmed by the $^1$H-NMR spectrum.

EXAMPLE 2

A mixture of 20.4 g of 2-methyl-2,4-diacetoxybut-3-enal and 14 g of 2-methyl-4,4-diacetoxybut-2-enal was heated with acetic acid containing 2.62% by weight of water for 2 hours at 100° C. The acetic acid and water were stripped off in a rotary evaporator, and the residue was then fractionally distilled to give 17 g (49%, based on methyldiacetoxybutenals employed) of 2-methyl-4,4-diacetoxybut-2-enal of boiling point 85°–93° C./0.4 mbar and 4.5 g (27%, based on methyldiacetoxybutenals employed) of 3-methyl-2,5-dihydrofuran-2-one of boiling point 45°–50° C./0.4 mbar.

EXAMPLE 4

A mixture of 2.9 g of 2-methyl-2,4-diacetoxybut-3-enal and 1.5 g of 2-methyl-4,4-diacetoxybut-2-enal was dissolved in 50 g of acetic acid which contained 0.025 g of concentrated sulfuric acid, and the mixture was stirred for 20 minutes at 100° C., under nitrogen. Thereafter, the sulfuric acid was neutralized with solid sodium bicarbonate, the acetic acid was stripped off in a rotary evaporator and the residue was distilled (70°–150° C./1 mbar) in a ball tube. 1.1 g (51%, based on methyldiacetoxybutenals employed) of 3-methyl-2,5-dihydrofuran-2-one, but no 2-methyl-4,4-diacetoxybut-2-enal, was obtained.

COMPARATIVE EXAMPLE 2

A mixture of 2.8 g of 2-methyl-2,4-diacetoxybut-3-enal and 1.5 g of 2-methyl-4,4-diacetoxybut-2-enal was dissolved in 50 g of glacial acetic acid, and the mixture was heated in the presence of 0.05 g of p-toluenesulfonic acid for 4 hours at 100° C. Gas chromatography showed that the reaction mixture contained 3-methyl-2,5-dihydrofuran-2-one as the principal product, but 2-methyl-4,4-diacetoxybut-2-enal was not detectable.

We claim:

1. A process for the preparation of a 2-alkyl-4,4-diacyloxybut-2-enal of the formula

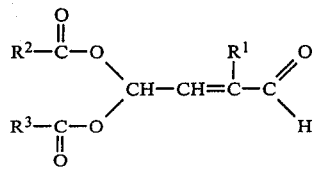

where $R^1$ is alkyl of 1 to 5 carbon atoms and $R^2$ and $R^3$ are each hydrogen, an aliphatic radical of 1 to 15 carbon atoms, a cycloaliphatic radical of 5 to 7 carbon atoms or an aromatic radical, which process comprises:
rearranging a 2-alkyl-2,4-diacyloxybut-3-enal of the formula

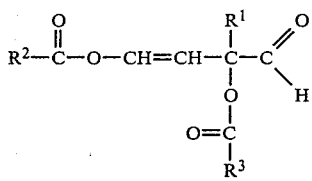

where $R^1$, $R^2$ and $R^3$ have the above meanings, into the product I by treatment with an aliphatic carboxylic acid in the absence of strong acids at a temperature of about 20° to 200° C. and for a treatment period of about 0.5 to 40 hours.

2. A process as claimed in claim 1, wherein the aliphatic carboxylic acid is selected from the group consisting of formic acid, acetic acid, propionic acid, butyric acid, valeric acid and stearic acid.

3. A process as claimed in claim 1 wherein $R^3$ of said starting material II and the product I is selected from the group consisting of alkyl of 1 to 18 carbon atoms, cycloalkyl of 5 to 7 carbon atoms and phenyl.

4. A process as claimed in claim 3 wherein the aliphatic acid being used is selected from the group consisting of formic acid, acetic acid, propionic acid, butyric acid, valeric acid and stearic acid.

5. A process as claimed in claim 1 wherein the aliphatic acid contains up to not more than 20 moles of water per mole of the reactant II.

6. A process as claimed in claim 1 wherein the aliphatic acid contains up to not more than 5 moles of water per mole of the reactant II.

7. A process as claimed in claim 1 wherein the rearrangement reaction is carried out at a temperature of about 50° to 120° C.

8. A process as claimed in claim 3 wherein the rearrangement reaction is carried out at a temperature of about 50° to 120° C.

9. A process as claimed in claim 1 wherein the treatment mixture contains from about 1 to 20% by weight of the reactant II undergoing rearrangmement.

10. A process as claimed in claim 3 wherein the treatment mixture contains from about 1 to 20% by weight of the reactant II undergoing rearrangement.

11. A process as claimed in claim 1 wherein the reactant II is dissolved in the aliphatic carboxylic acid which contains 0 to 20 moles of water per mole of the reactant II, the resulting solution is then heated at the temperature and for the period of time required for rearrangement, and upon completion of the rearrangement reaction, the carboxylic acid and any water is distilled off and the residue is purified by distillation or crystallization.

12. A process as claimed in claim 11 wherein the carboxylic acid being used is selected from the group consisting of formic acid, acetic acid, propionic acid, butyric acid, valeric acid and stearic acid.

13. A process as claimed in claim 11 wherein the carboxylic acid is glacial acetic acid.

14. A process as claimed in claim 11 wherein the carboxylic acid is an aqueous acetic acid.

* * * * *